(12) United States Patent
Corl

(10) Patent No.: US 9,717,475 B2
(45) Date of Patent: Aug. 1, 2017

(54) ULTRASOUND CATHETER FOR IMAGING AND BLOOD FLOW MEASUREMENT

(71) Applicant: Volcano Corporation, San Diego, CA (US)

(72) Inventor: Paul Douglas Corl, Palo Alto, CA (US)

(73) Assignee: Volcano Corporation, San Diego, CA (US)

( * ) Notice: Subject to any disclaimer, the term of this patent is extended or adjusted under 35 U.S.C. 154(b) by 781 days.

(21) Appl. No.: 13/892,062

(22) Filed: May 10, 2013

(65) Prior Publication Data

US 2013/0303920 A1  Nov. 14, 2013

Related U.S. Application Data

(60) Provisional application No. 61/646,074, filed on May 11, 2012, provisional application No. 61/747,469, filed on Dec. 31, 2012.

(51) Int. Cl.
*A61B 8/14* (2006.01)
*A61B 8/12* (2006.01)
(Continued)

(52) U.S. Cl.
CPC .......... *A61B 8/12* (2013.01); *A61B 8/44* (2013.01); *A61B 8/445* (2013.01); *A61B 8/4444* (2013.01);
(Continued)

(58) Field of Classification Search
CPC ....... A61B 8/4461; A61B 8/4483; A61B 8/00; A61B 8/4494; A61B 8/54; A61B 8/56; A61B 8/52; A61B 8/445; A61B 8/12
See application file for complete search history.

(56) References Cited

U.S. PATENT DOCUMENTS

| | | | |
|---|---|---|---|
| 5,000,185 A | 3/1991 | Yock | |
| 2001/0016688 A1* | 8/2001 | Moore | A61B 8/12 600/466 |

(Continued)

FOREIGN PATENT DOCUMENTS

| | | |
|---|---|---|
| JP | 2006 319713 A | 11/2006 |
| WO | WO 2011/013053 A1 | 2/2011 |

OTHER PUBLICATIONS

International Searching Authority/KIPO, "Notification of Transmittal of the International Search Report and The Written Opinion of the International Searching Authority, or the Declaration," for PCT/US2013/040642, mailed Aug. 27, 2013, 18 pages.

(Continued)

*Primary Examiner* — Elmer Chao

(57) ABSTRACT

Rotational intravascular ultrasound (IVUS) imaging devices, systems, and methods are provided. Some embodiments are directed to transducer mounting configurations that enable polymer piezoelectric micro-machined ultrasonic transducers (PMUTs) to be used with a Doppler color flow rotational IVUS imaging system. In one embodiment, a rotational intravascular ultrasound (IVUS) device includes: a flexible elongate body; a piezoelectric micromachined ultrasound transducer (PMUT) coupled to a distal portion of the flexible elongate body; and an application-specific integrated circuit (ASIC) coupled to the distal portion of the flexible elongate body. The ASIC is electrically coupled to the PMUT and includes a pulser, an amplifier, a protection circuit, and timing and control circuitry for coordinating operation of the pulser, amplifier, and protection circuit. The PMUT transducer is mounted with a tilt angle such that the IVUS catheter can be used to collect Doppler ultrasound blood flow data in conjunction with the IVUS imaging.

14 Claims, 8 Drawing Sheets

(51) Int. Cl.
  *A61B 8/00* (2006.01)
  *A61B 8/08* (2006.01)
  *B06B 1/06* (2006.01)

(52) U.S. Cl.
  CPC .......... *A61B 8/4461* (2013.01); *A61B 8/4483* (2013.01); *A61B 8/488* (2013.01); *B06B 1/06* (2013.01); *Y10T 29/42* (2015.01)

(56) References Cited

U.S. PATENT DOCUMENTS

| | | |
|---|---|---|
| 2005/0203416 A1 | 9/2005 | Angelsen et al. |
| 2005/0228290 A1* | 10/2005 | Borovsky ................ A61B 8/12 600/466 |
| 2006/0052707 A1* | 3/2006 | Dickinson ................ A61B 8/12 600/466 |
| 2006/0173350 A1 | 8/2006 | Yuan et al. |
| 2008/0134793 A1 | 6/2008 | Woychik et al. |
| 2009/0076390 A1 | 3/2009 | Lee et al. |
| 2009/0131798 A1 | 5/2009 | Minar et al. |
| 2009/0177093 A1* | 7/2009 | Zelenka ................... A61B 8/12 600/463 |
| 2010/0168583 A1 | 7/2010 | Dausch et al. |
| 2010/0179432 A1 | 7/2010 | Thornton |
| 2010/0234736 A1 | 9/2010 | Corl |
| 2011/0009750 A1* | 1/2011 | Taylor ................... A61B 18/245 600/463 |
| 2011/0313290 A1 | 12/2011 | Weekamp et al. |

OTHER PUBLICATIONS

Extended European Search Report for EP Application No. 13787619.9, mailed Jan. 8, 2016, 11 pages.

\* cited by examiner

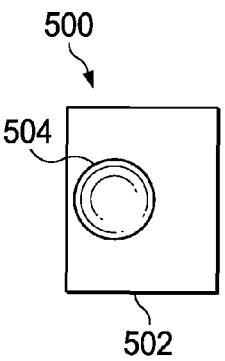
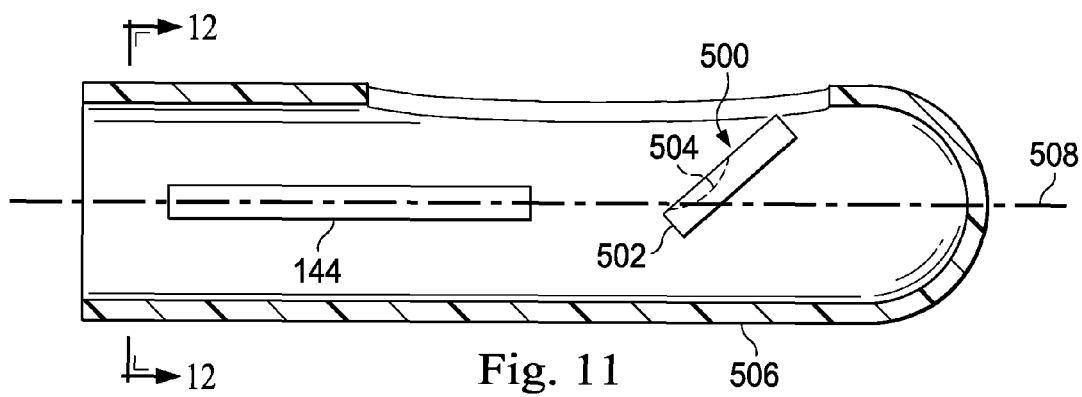
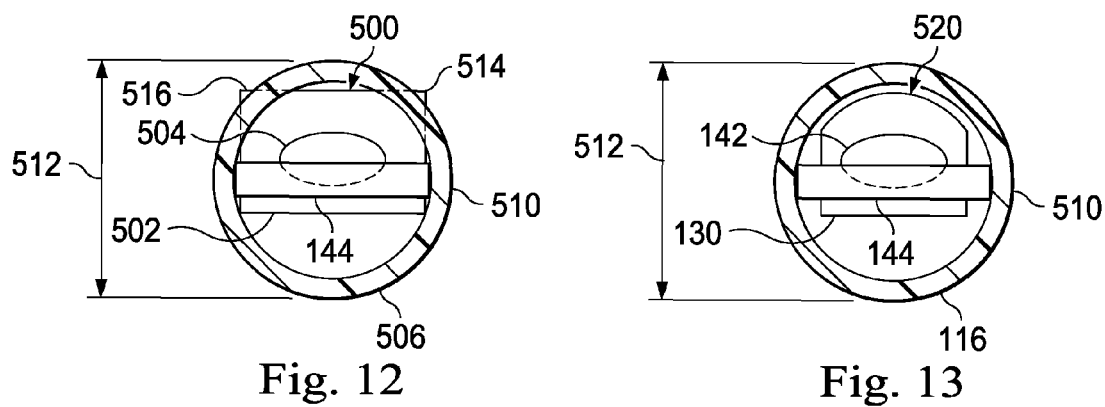

ULTRASOUND CATHETER FOR IMAGING AND BLOOD FLOW MEASUREMENT

CROSS-REFERENCE TO RELATED APPLICATIONS

This application claims the benefit of U.S. Provisional Application No. 61/646,074, filed May 11, 2012, and U.S. Provisional Application No. 61/747,469, filed Dec. 31, 2012, each of which is hereby incorporated by reference in its entirety.

TECHNICAL FIELD

The present disclosure relates generally to intravascular ultrasound imaging inside the living body and, in particular, to an intravascular ultrasound imaging catheter that relies on a mechanically-scanned ultrasound transducer, including embodiments where the transducer is a piezoelectric micromachined ultrasound transducer based on a polymer piezoelectric material. The present disclosure describes polymer piezoelectric micromachined ultrasound transducer and catheter configurations that are particularly well suited to simultaneously forming a cross-sectional image of a blood vessel and measuring the blood flow velocity within the vessel. A PMUT using polymer piezoelectric material suitable for IVUS imaging is not capable of efficiently driving the long electrical cable from the distal end of the catheter back to the patient interface module at the proximal end of the catheter. Therefore, the PMUT requires active electronics (an amplifier circuit) closely coupled to the transducer. The present disclosure provides transducer structural designs and mounting arrangements that are particularly well-suited for utilizing a polymer-based PMUT within a rotational IVUS imaging system.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. IVUS imaging uses ultrasound echoes to form a cross-sectional image of a vessel of interest. Typically, an ultrasound transducer on an IVUS catheter both emits ultrasound pulses and receives the reflected ultrasound echoes. The ultrasound waves pass easily through most tissues and blood, but they are partially reflected from discontinuities arising from tissue structures (such as the various layers of the vessel wall), red blood cells, and other features of interest. The IVUS imaging system, which is connected to the IVUS catheter by way of a patient interface module (PIM), processes the received ultrasound echoes to produce a cross-sectional image of the vessel where the transducer is located.

To establish the need for treatment, the IVUS system is used to measure the lumen diameter or cross-sectional area of the vessel. For this purpose, it is important to distinguish blood from vessel wall tissue so that the luminal border can be accurately identified. In an IVUS image, the blood echoes are distinguished from tissue echoes by slight differences in the strengths of the echoes (e.g., vessel wall echoes are generally stronger than blood echoes) and from subtle differences in the texture of the image (i.e., speckle) arising from structural differences between blood and vessel wall tissue. As IVUS imaging has evolved, there has been a steady migration towards higher ultrasound frequencies to improve the resolution. But as ultrasound frequency is increased, there is diminished contrast between the blood echoes and vessel wall tissue echoes. At the 20 MHz center frequency used in early generations of IVUS, the blood echoes were noticeably weak in comparison to the vessel wall echoes due to the small size of the red blood cell compared to the acoustic wavelength. However, at the 40 MHz ultrasound center frequency now commonly used for IVUS imaging, there is only a modest difference between blood and tissue echoes as the ultrasound wavelength approaches the dimensions of a red blood cell.

Another use of IVUS imaging in interventional cardiology is to help identify the most appropriate course of treatment. For example, IVUS imaging may be used to assist in recognizing the presence of a mural thrombus (i.e., coagulated blood attached to the vessel wall and stationary within the blood vessel) in an artery prior to initiating treatment. If a thrombus is identified in a region where disease has caused a localized narrowing of the arterial lumen, then the treatment plan might be modified to include aspiration (i.e., removal) of the thrombus prior to placing a stent in the artery to expand and stabilize the vessel lumen. In addition, the identification of a thrombus could lead the physician to order a more aggressive course of anti-coagulant drug therapy to prevent the subsequent occurrence of potentially deadly thrombosis. In a conventional IVUS image, however, there is very little difference in appearance between a thrombus and moving blood.

Another use of IVUS imaging in interventional cardiology is to visualize the proper deployment of a stent within an artery. A stent is an expandable mesh cylinder that is generally deployed within the artery to enlarge and/or stabilize the lumen of the artery. The expansion of the stent typically stretches the vessel wall and displaces the plaque that otherwise forms a partial obstruction of the vessel lumen. The expanded stent forms a scaffold, propping the vessel lumen open and preventing elastic recoil of the vessel wall after it has been moderately stretched. In this context, it is important to recognize proper stent apposition; that is, the stent struts should be pressed firmly against the vessel wall. A poorly deployed stent may leave stent struts in the stream of the blood flow and these exposed stent struts are prone to initiate thrombus formation. Thrombus formation following stent deployment is referred to as "late stent thrombosis" and these thrombi can occlude the stented location or break free from the stent strut to occlude a downstream branch of a coronary artery and trigger a heart attack.

In these examples of IVUS imaging, it is particularly useful to identify moving blood, and to distinguish the moving blood from the relatively stationary tissue or thrombi. Motion information can be helpful in delineating the interface between blood and vessel wall so that the lumen border can be more easily and accurately identified. Motion parameters such as velocity may be the most robust ultrasound-detectable parameters for distinguishing moving blood from a stationary thrombus. In the case of stent malapposition, the observation of moving blood behind a stent strut is a clear indication that the stent strut is not firmly pressed against the vessel wall as it should be, possibly indicating a need to further expand the stent. In each of the aforementioned IVUS imaging examples, the addition of motion parameters to the traditional IVUS display of echo amplitude can improve the diagnosis and treatment of a patient.

There are two types of IVUS catheters in common use today: solid-state and rotational, with each having advantages and disadvantages. Solid-state IVUS catheters use an array of ultrasound transducers (typically 64) distributed around the circumference of the catheter and connected to an electronic multiplexer circuit. The multiplexer circuit selects array elements for transmitting an ultrasound pulse and receiving the echo signal. By stepping through a sequence of transmit-receive pairs, the solid-state IVUS system can synthesize the effect of a mechanically scanned transducer element, but without moving parts. Since there is no rotating mechanical element, the transducer array can be placed in direct contact with the blood and vessel tissue with minimal risk of vessel trauma and the solid-state scanner can be wired directly to the imaging system with a simple electrical cable and a standard detachable electrical connector.

In a typical rotational IVUS catheter, a single ultrasound transducer element fabricated from a piezoelectric ceramic material is located at the tip of a flexible driveshaft that spins inside a plastic sheath inserted into the vessel of interest. The transducer element is oriented such that the ultrasound beam propagates generally perpendicular to the axis of the catheter. The fluid-filled sheath protects the vessel tissue from the spinning transducer and driveshaft while permitting ultrasound waves to freely propagate from the transducer into the tissue and back. As the driveshaft rotates (typically at 30 revolutions per second), the transducer is periodically excited with a high voltage pulse to emit a short burst of ultrasound. The same transducer then listens for the returning echoes reflected from various tissue structures, and the IVUS imaging system assembles a two dimensional display of the vessel cross-section from a sequence of several hundred of these ultrasound pulse/echo acquisition sequences occurring during a single revolution of the transducer.

While the solid-state IVUS catheter is simple to use, thanks to its lack of moving parts, it cannot match the image quality available from a rotational IVUS catheter. It is difficult to operate a solid-state IVUS catheter at the same high frequency as a rotational IVUS device, and the lower operating frequency of solid-state IVUS catheters translates into poorer resolution compared to that of a higher frequency rotational IVUS catheter. There are also artifacts such as sidelobes, grating lobes, and poor elevation focus (perpendicular to the imaging plane) that arise from the array-based imaging that are greatly reduced or completely absent with a rotational IVUS device. Despite the image quality advantages of the rotational IVUS catheter, each of these devices has found a niche in the interventional cardiology market, with solid-state IVUS preferred in circumstances where ease-of-use is paramount and the reduced image quality is acceptable for the particular diagnostic needs, while rotational IVUS is preferred where image quality is paramount and the more time-consuming catheter preparation is justified.

Traditionally, IVUS catheters, whether rotational or solid-state catheters, are side-looking devices, wherein the ultrasound pulses are transmitted substantially perpendicular to the axis of the catheter to produce a cross-sectional image representing a slice through the blood vessel. The blood flow in the vessel is normally parallel to the axis of the catheter and perpendicular to the plane of the image. IVUS images are typically presented in a grey-scale format, with strong reflectors (vessel boundary, calcified tissue, metal stents, etc.) displayed as bright (white) pixels, with weaker echoes (blood and soft tissue) displayed as dark (grey or black) pixels. Thus, flowing blood and static blood (i.e., thrombi) may appear very similar in a traditional IVUS display.

In ultrasound imaging applications, Doppler ultrasound methods are often used to measure blood and tissue velocity, and the velocity information is used to distinguish moving blood echoes from stationary tissue echoes. Commonly, the velocity information is used to colorize the grey-scale ultrasound image in a format referred to as Doppler color flow ultrasound imaging, with fast moving blood tinted red or blue, depending on its direction of flow, and with slow moving or stationary tissue displayed in grey-scale.

Traditionally, IVUS imaging has not been amenable to Doppler color flow imaging since the direction of blood flow is predominantly perpendicular to the IVUS imaging plane. More specifically, Doppler color flow imaging and other Doppler techniques do not function well when the velocity of interest (i.e., blood flow velocity) is perpendicular to the imaging plane and perpendicular to the direction of ultrasound propagation, resulting in near zero Doppler shift attributable to blood flow. In the case of rotational IVUS, there is an added complication due to the continuous rotation of the transducer, which makes it problematic to collect the multiple echo signals from the same volume of tissue needed to make an accurate estimate of the velocity-induced Doppler shift.

In the case of solid-state IVUS, the problem of low Doppler shift has been overcome to some extent by the development of an alternative (non-Doppler) method for blood motion detection. The ChromaFlo method (U.S. Pat. No. 5,921,931) uses an image correlation method instead of Doppler to identify moving blood. Image correlation techniques for motion detection are generally inferior to Doppler methods, and in particular, are not suitable for rotational IVUS since the rate of decorrelation attributable to the rotating ultrasound beam is comparable to the rate of decorrelation due to the blood flow. Solid-state IVUS catheters avoid this rotating beam problem by electronically maintaining a constant beam direction for a sequence of pulses before electronically incrementing the beam direction to the next image angle.

In U.S. Provisional Patent Application No. 61/646,080 entitled "Device and System for Imaging and Blood Flow Velocity Measurement," filed May 11, 2012 and incorporated by reference herein in its entirety, there is described a rotational IVUS catheter configuration and an IVUS imaging system architecture capable of overcoming the aforementioned obstacles to Doppler color flow imaging. A key aspect of the invention is that the ultrasound transducer is tilted such that the ultrasound beam emerges from the catheter at a substantial angle with respect to a perpendicular to the catheter axis.

In U.S. Provisional Patent Application No. 61/646,062 entitled "Circuit Architecture and Electrical Interface for an Advanced Rotational IVUS Catheter" filed on May 11, 2012 and incorporated by reference herein in its entirety, there is further described an advanced transducer technology capable of providing superior IVUS image quality compared to that available from the traditional rotational IVUS catheter utilizing lead-zirconate-titanate (PZT) piezoelectric ceramic transducer technology. The piezoelectric micromachined ultrasound transducer (PMUT) fabricated using a polymer piezoelectric material, also disclosed in U.S. Pat. No. 6,641,540, hereby incorporated by reference in its entirety, offers greater than 100% bandwidth for optimum resolution in the radial direction, and a spherically-focused aperture for optimum azimuthal and elevation resolution. While this polymer PMUT technology promises significant image quality advantages, the inherently planar silicon wafer fabrication process for manufacturing these advanced transducers makes it difficult to achieve the substantial tilt angle required for Doppler color flow imaging in the relatively small area available with an IVUS catheter.

Accordingly, there is a need for improved devices, systems, and methods for providing a polymer piezoelectric micro-machined ultrasonic transducer and rotational IVUS catheter configuration providing the required transducer tilt angle and other features to render it suitable for use with a Doppler color flow intravascular ultrasound imaging system.

SUMMARY

Embodiments of the present disclosure describes a polymer piezoelectric micro-machined ultrasonic transducer and rotational IVUS catheter configuration providing a transducer tilt angle and other features to render it suitable for use with a Doppler color flow intravascular ultrasound imaging system.

One aspect of the present disclosure is to facilitate Doppler color flow imaging, wherein velocity data is encoded as a color overlay of the gray scale IVUS image to enhance the differentiation between moving blood echoes and stationary tissue echoes.

Another aspect of the present disclosure is to facilitate blood echo suppression—hiding the echoes that contain a significant velocity component such that the vessel lumen appears empty or darker than normal, thereby enhancing the distinction between the blood-filled lumen and the vessel wall.

Another aspect in one embodiment is to facilitate automated border detection—using the velocity information to improve the algorithm for automatic (computer-based) detection of the lumen border.

In yet another aspect of one embodiment, the system provides ECG-gated Doppler color flow images. In the coronary arteries, it is advantageous to use an ECG (electrocardiogram) trigger to select the diastolic portion of the heart cycle for detailed analysis, since that is the phase of the cardiac cycle where the blood flow is highest and the tissue motion is lowest, thereby providing the best differentiation between the moving blood and stationary tissue.

In still a further aspect of one embodiment, the system facilitates thrombus detection—using the velocity information to improve the differentiation between generally stationary coagulated blood (thrombus) and moving blood.

In a further aspect, the system facilitates quantitative blood flow estimation—integration of the blood velocity over the cross section of the vessel lumen to provide a quantitative measurement of volumetric blood flow. Blood flow calculation provides functional parameter to supplement the anatomic measurements provided by the IVUS image. Although not required, the use of a pharmacologic agent such as Adenosine to stimulate maximum hyperemia in the vessel can facilitate the calculation of coronary flow reserve, an important diagnostic value.

In another aspect, the system facilitates wide dynamic range IVUS—the same pulse sequence used to provide the information needed for measuring Doppler frequency shift can also be used to extend the dynamic range of the IVUS signals, making it easy to detect the weak echoes from soft tissue while simultaneously detecting the strong echoes from metal stent struts or calcified plaques embedded in the vessel wall.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 10 is a diagrammatic top view of a PMUT MEMS component according to an embodiment of the present disclosure.

FIG. 11 is a diagrammatic, cross-sectional side view of a distal portion of an imaging device incorporating the PMUT MEMS component of FIG. 10 according to an embodiment of the present disclosure.

FIG. 12 is a diagrammatic, cross-sectional end view of the distal portion of the imaging device of FIG. 11 taken along section line 12-12.

FIG. 13 is a diagrammatic, cross-sectional end view of the distal portion of an imaging device similar to those of FIGS. 6-9 according to an embodiment of the present disclosure.

DETAILED DESCRIPTION

Figure 1:
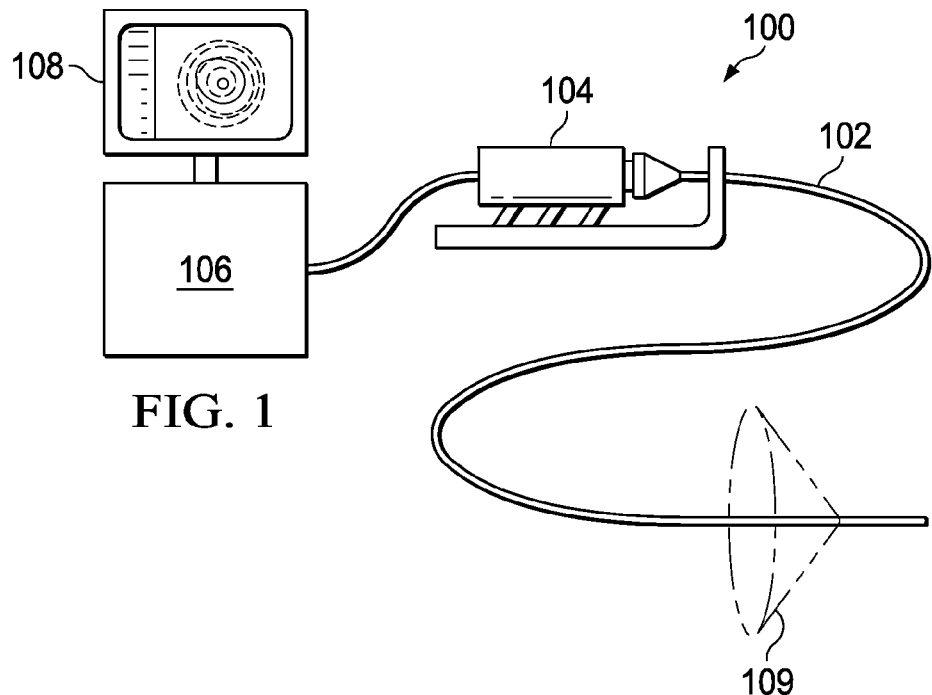
FIG. 1 is an overview of the Doppler color flow rotational IVUS imaging system according to an embodiment of the present disclosure.

For the purpose of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

To advance the clinical utility of IVUS imaging, it is desirable to provide improved image quality by incorporating an advanced ultrasound transducer technology to replace the traditional lead-zirconate-titanate (PZT) piezoelectric ceramic transducer. The piezoelectric micromachined ultrasound transducer (PMUT) fabricated on a microelectromechanical system (MEMS) substrate using a polymer piezoelectric material, for example as disclosed in U.S. Pat. No. 6,641,540, which is hereby incorporated by reference in its entirety, offers broad bandwidth (>100%) and a spherically-focused aperture. The broad bandwidth and correspondingly compact transducer impulse response provides optimum resolution in the radial dimension, while the spherically-focused aperture provides optimum resolution in the lateral and elevation dimensions. The improved resolution provided by this advanced ultrasound transducer design facilitates better diagnostic accuracy, enhances the ability to discern different tissue types, and improves the ability to accurately ascertain the borders of the vessel lumen. A practical implementation for a polymer PMUT suitable for mounting in a rotational IVUS catheter is detailed further in U.S. Provisional Patent Application No. 61/646,062 entitled "Circuit Architecture and Electrical Interface for Rotational Intravascular Ultrasound (IVUS) Devices, filed May 11, 2012 and hereby incorporated by reference in its entirety. The aforementioned application describes various configurations for combining the needed electronic circuitry with the PMUT device.

The capability of the rotational IVUS device can be further enhanced by adding Doppler color flow imaging feature to the gray-scale IVUS imaging-only technology provided by the traditional IVUS imaging system and catheter. The Doppler color flow capable IVUS imaging system and catheter technology are described in U.S. Provisional Patent Application No. 61/646,080 entitled "Device and System for Imaging and Blood Flow Velocity Measurement" filed on May 11, 2012 and hereby incorporated by reference in its entirety. A key feature of the Doppler-capable IVUS catheter is to have the transducer tilted such that the ultrasound beam emerges from the catheter at a modest angle with respect to a perpendicular to the axis of the catheter. This application discloses several ultrasound mounting configurations that allow the PMUT transducer to be mounted at the appropriate tilt angle to facilitate the collection of Doppler ultrasound blood flow data and the subsequent display of Doppler color flow IVUS images.

An overview of the Doppler color flow rotational IVUS imaging system is shown in FIG. 1. The main components of a rotational IVUS imaging system are the rotational IVUS catheter, the IVUS system with its associated patient interface module (PIM), and a monitor to display the IVUS image. The key elements of the invention which distinguish it from a traditional rotational IVUS imaging system include a modified (Doppler-enabled) rotational IVUS catheter 102, a Doppler-capable IVUS imaging system 106 with associated patient interface module (PIM) 104, and a color monitor 108 to display the Doppler color flow IVUS image. In particular, the Doppler Color Flow Rotational IVUS Imaging System requires a modified rotational IVUS catheter 102 which includes an ultrasound transducer tilted at a modest angle away from a perpendicular to the axis of the catheter to provide a shallow conical imaging surface 109 instead of the traditional imaging plane which is nominally perpendicular to the axis of the catheter and the axis of the blood vessel. More in particular, the ultrasound transducer of the present invention is a piezoelectric micromachined ultrasound transducer based on a polymer piezoelectric material.

Figure 2:
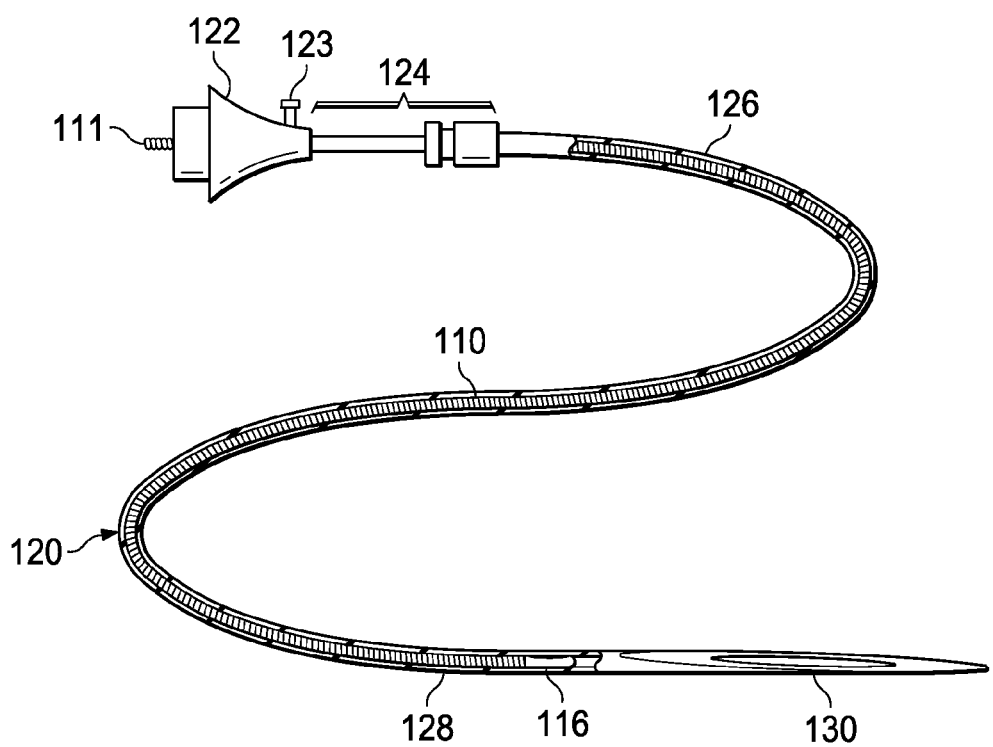
FIG. 2 is an overview of a rotational IVUS catheter, which can be optimized for Doppler color flow IVUS imaging.

FIG. 2 shows a more detailed overview of the modified rotational IVUS catheter 102, optimized for Doppler color flow IVUS imaging. In many respects, this catheter is similar to traditional rotational IVUS catheters, such as the Revolution® catheter available from Volcano Corporation and described in U.S. Pat. No. 8,104,479, or those disclosed in U.S. Pat. Nos. 5,243,988 and 5,546,948, each of which is hereby incorporated by reference in its entirety. In that regard, a rotational IVUS catheter typically includes an imaging core 110 and an outer catheter/sheath assembly 120. The rotating imaging core 110 includes a rotational interface 111 to provide electrical and mechanical coupling to the PIM, a flexible driveshaft composed of two or more layers of counter wound stainless steel wires, an electrical cable threaded through the inner lumen of the flexible driveshaft, a transducer housing 116 attached to the end of the flexible driveshaft, and an ultrasound transducer mounted within said housing 116. The outer catheter/sheath assembly 120 includes a proximal bearing, a telescoping section, a proximal shaft, a window segment, and a tip assembly. The proximal bearing 122 supports the rotational interface 111 of the imaging core 110, and it may include a port 123 for injecting saline into the lumen of the catheter/sheath assembly and a fluid seal to prevent the fluid from leaking out of the proximal end of the assembly. The telescoping section 124 permits the catheter/sheath assembly to be extended in length, causing the imaging core to be pulled back relative to the sheath. This operation facilitates longitudinal pullback of the transducer at the tip of the imaging core through a length of vessel that is being examined by IVUS, thereby enabling the system to collect a full set of three-dimensional ultrasound image data. The proximal shaft 126 is a robust, flexible tubular structure that extends from the telescoping section to the window section of the assembly. The window section (or sheath) 128 is an extension of the proximal shaft, but it is formed of a material that has an acoustic impedance and sound speed particularly well-suited for conducting the ultrasound beam from the transducer out into the blood vessel with minimal reflection, attenuation, or beam distortion. The tip assembly 130 is attached beyond the window segment and it provides a short segment of catheter designed to engage with a conventional coronary guidewire so that the IVUS catheter can be easily directed into the vessel of interest, or easily removed from the guidewire for a catheter exchange.

Figure 3A:
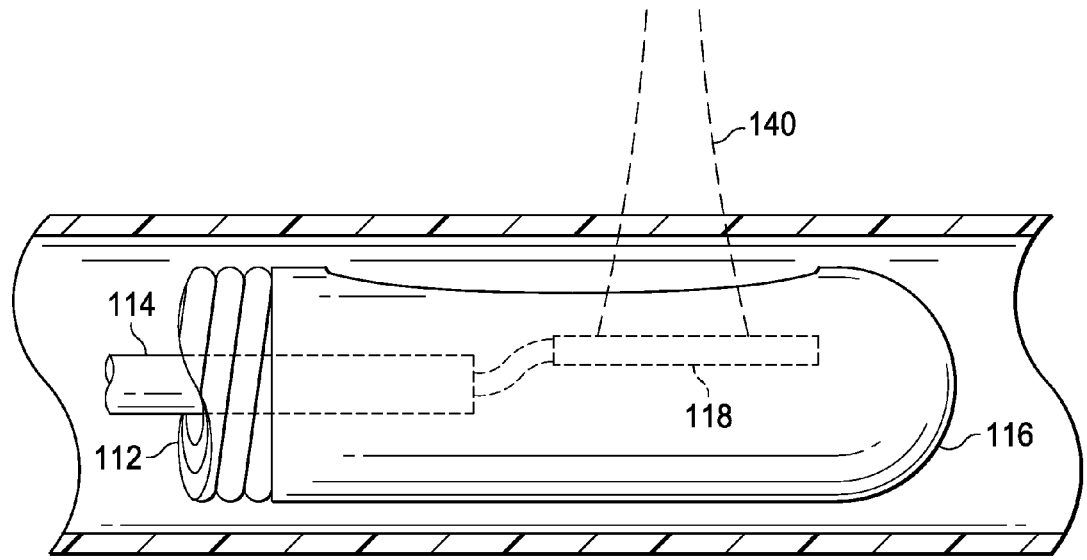
FIG. 3A is a detailed illustration of a prior art style transducer assembly suitable for IVUS imaging only, without Doppler ultrasound flow measurement capability.

FIG. 3A illustrates an ultrasound transducer configuration in a prior art rotational IVUS catheter. In the prior art device, the transducer 118 is typically mounted substantially in line with the catheter axis such that the ultrasound beam emerges substantially perpendicular to the axis of the catheter, and therefore this prior art device is suitable for traditional IVUS imaging only, and not for Doppler color flow imaging. In practice, the transducer is frequently mounted at a slight tilt angle in order to reduce the strength of the echo and reverberations from the catheter sheath. The echo (and reverberations) received by the transducer element from the catheter sheath are strongest when the sheath surface is parallel to the transducer face such that the echoes from different portions of the sheath arrive back at the transducer in phase with one another. If the transducer surface is tilted at an angle such that there is at least one wavelength of path length difference across the axial length of the transducer, then the echoes from the different portions of the sheath will tend to cancel and the echo will be reduced. As an example of the degree of transducer tilt preferred for a conventional rotational IVUS catheter, the aperture width for a typical rotational IVUS catheter is approximately 12 wavelengths (for example, a 500 um transducer length and ~40 um wavelength at a 40 MHz transducer center frequency). To introduce one wavelength of round trip path length difference across the aperture would require one-half wavelength of tilt over the same width, or an angle of approximately ¹⁄₂₄ radian) (~2.5°. With optimum sheath design, the sheath reflection can be small enough that no transducer tilt is needed. Transducer tilt angles in the range of 0 to 8° are common for conventional rotational IVUS catheters. Other prior art devices use a transducer oriented to emit an ultrasound beam parallel to the catheter axis, but then incorporate a mirror assembly to deflect the beam so that once again, the ultrasound beam emerges substantially perpendicular to the axis of the catheter.

Figure 3B:
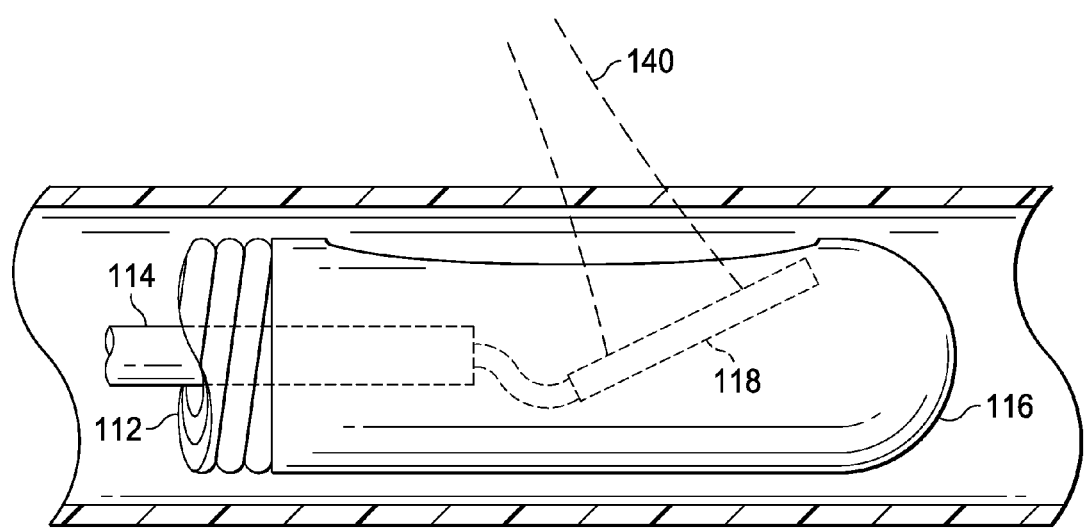
FIG. 3B is a detailed illustration of a transducer assembly suitable for IVUS imaging with Doppler ultrasound flow measurement capability.

FIG. 3B illustrates the same detail with regard to the ultrasound transducer configuration in a catheter optimized for Doppler color flow imaging as described in co-pending application discussed above. In this case the transducer 118 in the Doppler-enabled rotational IVUS catheter is tilted significantly, such that the ultrasound beam emerges from the catheter at a modest angle of 10° to 30° with respect to a perpendicular to the catheter axis, and more preferably at a tilt angle of 15° to 25°. FIG. 3B shows the transducer tilted toward the proximal end of the catheter, but the tilt could be in the opposite direction as well, toward the distal end of the catheter.

To facilitate the collection of Doppler ultrasound echo information, the ultrasound transducer 118 should be mounted at a substantial tilt angle with respect to the axis of the catheter, and more in particular with respect to the present disclosure, the ultrasound transducer 118 is preferably a PMUT device fabricated on a microelectromechanical system (MEMS) substrate using a polymer piezoelectric material, and packaged together with its associated application-specific integrated circuit (ASIC) as detailed in U.S. Provisional Patent Application No. 61/646,062 entitled "Circuit Architecture and Electrical Interface for Rotational Intravascular Ultrasound (IVUS) Devices," filed May 11, 2012 and hereby incorporated by reference in its entirety.

There are two competing considerations for choosing the transducer tilt angle for this device: (1) the larger the tilt angle, the greater will be the Doppler component in the ultrasound echo, and (2) the larger the tilt angle, the greater will be the geometric distortion when a conical imaging surface is projected onto a planar display. The Doppler shift measured by an ultrasound system is proportional to the cosine of the angle between the direction of the motion and the direction of propagation of the ultrasound beam. In the idealized circumstance, where the axis of the catheter is aligned with the axis of the vessel, and where the velocity of blood flow is parallel to the axis of the vessel as well, the angle between the direction of blood flow and the direction of the ultrasound beam is the complement of the transducer tilt angle. In this case, the Doppler shift will be proportional to the sine of the transducer tilt angle. For a zero tilt angle, there is no Doppler shift at all, and the velocity information cannot be obtained from traditional Doppler signal processing. The theoretical maximum Doppler shift would be obtained with a transducer tilt angle of 90°, but that would preclude the possibility for IVUS imaging since the ultrasound beam would then be aligned with the axis of rotation. At a modest tilt angle of 30°, the Doppler shift would be 50% of the theoretical maximum, and a reasonable IVUS image from that shallow conical surface could still be obtained.

The choice of the transducer tilt angle for Rotational Doppler Color Flow IVUS imaging should also consider the robustness of the Doppler velocity measurement in the face of misalignment between the catheter axis and the axis of the blood vessel, as well as the ability to distinguish the Doppler shift of fast moving blood from the Doppler shift of slow moving tissue. In the course of normal clinical use, there may be misalignments between the axis of the catheter and the axis of the vessel (and the direction of the blood flow). If that misalignment is comparable to the transducer tilt angle, then the Doppler shift across a portion of the vessel lumen might be reduced to zero where the catheter misalignment cancels the transducer tilt angle. However, if the transducer tilt angle is significantly greater than the typical range for catheter misalignment, the system will retain a robust capability for estimating blood motion across the entire vessel lumen. The human anatomy often includes significant tortuosity in the coronary arteries where IVUS imaging is most commonly used, and it is difficult to predict the largest misalignment that can exist between the vessel axis and the catheter axis. However, an exemplary large misalignment that might be experienced in clinical practice would be the equivalent of the 1 mm diameter catheter traversing a 3 mm vessel lumen over a 10 mm length of vessel, corresponding to a likely maximum misalignment angle of approximately 12°. Over much of the epicardial arterial tree, the misalignment angle would be substantially less than this maximum likely value. Accordingly, it would be helpful for maintaining a robust Doppler signal if the transducer tilt angle was greater than 12°. Based on this consideration, the transducer tilt angle should be greater than 15° to allow a small margin above the 12° maximum likely misalignment angle predicted above. More preferably, the transducer tilt angle should be approximately 20° to provide a greater margin of tolerance for catheter to vessel misalignment.

For the intracoronary IVUS application, the Doppler velocity data is important for its role in helping to differentiate blood from tissue, hence the importance of distinguishing the Doppler shift of fast moving blood from the Doppler shift of slow moving tissue. In color flow imaging applications throughout most of the body (e.g., liver, carotid, or peripheral artery), the tissue motion is negligible, so the velocity threshold for classification of an echo as a moving blood echo can be very low. However in the case of coronary imaging, the tissue motion can be quite prominent, and it is more difficult to reliably distinguish tissue motion from blood flow. Although the motion of the heart muscle is quite rapid during early systole when the ventricles contract, the IVUS catheter tends to move with the heart by virtue of its capture within the coronary artery. Thus, the relative motion between the catheter and the surrounding tissue is usually significantly less than the absolute motion of the heart. An example of a fast movement of the IVUS catheter with respect to the heart would be for the catheter to shift one vessel diameter (~3 mm) during the approximately 100 msec that constitutes the early portion of systole. The corresponding relative tissue velocity in this case would be ~3 cm/sec. Throughout most of the cardiac cycle, and in the majority of locations throughout the epicardial arterial tree, the actual tissue velocity will be much less than this estimate. In particular, in the coronary arteries, blood flow is most significant (typically in the range of 10 cm/sec to 100 cm/sec) during diastole, the portion of the cardiac cycle when the heart motion is at its minimum (as the heart muscle gradually relaxes). Accordingly, in some embodiments, it is desirable to gate the Doppler color flow imaging with the ECG to capture blood flow measurements only during diastole, when the blood flow is maximum, and the heart motion (and relative tissue velocities) are at a minimum.

Besides the consideration of producing a robust Doppler signal, the other important consideration with respect to the transducer tilt angle is the geometric distortion it produces in the IVUS image. In the case of a tilted transducer mount, the ultrasound beam emerges from the catheter at an angle with respect to a perpendicular to the axis of the catheter, and as the imaging core rotates, the ultrasound beam sweeps out a conical imaging surface 109 to produce an ultrasound image of the vessel. Since the ultrasound image produced over this conical surface is typically displayed on a planar video monitor, there is a geometric distortion introduced in the conical to planar transformation. The degree of distortion can be quantified by a figure of merit which represents the discrepancy between radial and tangential distance measurements on the distorted planar display. The distortion figure of merit can be calculated as one minus the cosine of the tilt angle. A zero tilt angle produces a planar imaging surface with no distortion, while a tilt angle of 20° produces 6% distortion. A modest degree of distortion will not interfere with the qualitative interpretation of the image which requires the identification of the inner and outer borders of the vessel wall structures, and assessment of the general character of the echoes from lesions within the vessel wall. Any quantitative measurements, such as lumen diameter or plaque cross-sectional area to be made from the distorted planar display can be corrected by applying the appropriate mathematical formula during the measurement process to remove the conical distortion from the calculation. For the preferred range of tilt angles from 10° to 30°, the geometric distortion figure of merit ranges from 1.5% to 13%, while for the more preferred range of tilt angles from 15° to 25°, the visual distortion ranges from 3% to 9%

Figure 4A:
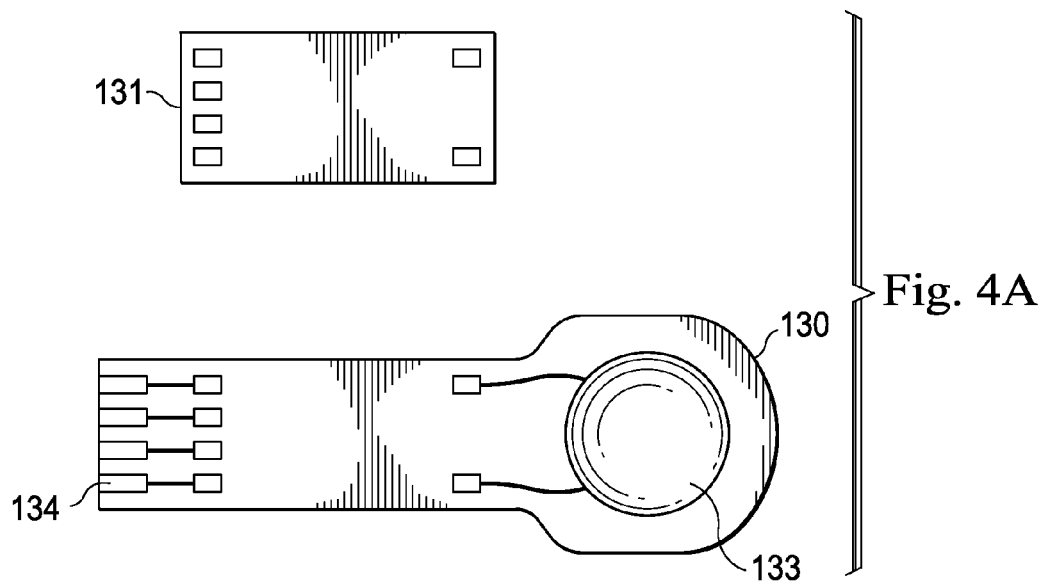
FIGS. 4A and 4B are illustrations of a polymer piezoelectric micromachined ultrasound transducer, including an electronic circuit mounted onto the transducer substrate.
Figure 4B:
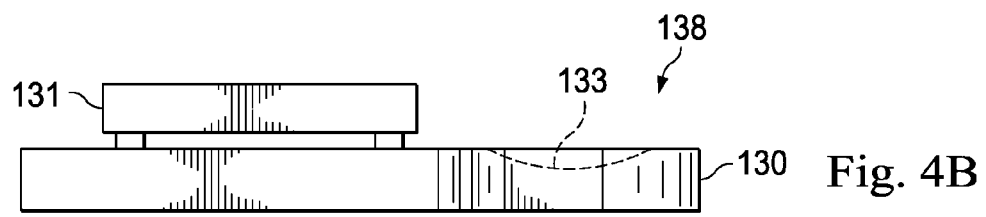

Referring now to FIGS. 4A and 4B, illustrated therein are aspects of the MEMS/ASIC hybrid assembly 138 which serves as the ultrasound transducer 118 in one embodiment of a PMUT-based rotational IVUS catheter. In this example, the MEMS 130 consists of a paddle-shaped silicon substrate supporting a spherically-focused transducer 133. The narrow portion of the substrate includes a set of electrical bond pads where the ASIC 131 is flip-chip bonded to the MEMS substrate 130. The ASIC contains electronic circuitry, possibly including cable interface, amplifier, high-voltage pulser, protection circuit, control logic, and/or power supply conditioning circuits used to interface the polymer-based PMUT transducer to rest of the IVUS imaging system. Additional bond pads 134 are included at the proximal end of the MEMS substrate for attachment of the electrical cable which carries electrical signals to the PIM.

Figure 4C:
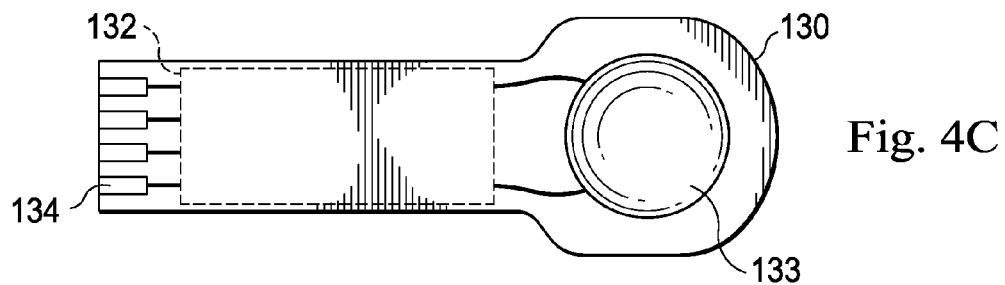
FIGS. 4C and 4D are illustrations of a polymer piezoelectric micromachined ultrasound transducer, including an electronic circuit fabricated within the silicon transducer substrate.
Figure 4D:
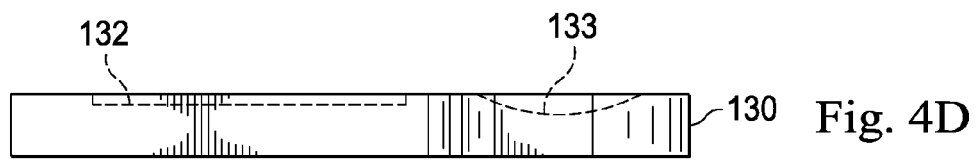

An alternative to the flip-chip bonded ASIC/MEMS hybrid assembly is illustrated in FIGS. 4C and 4D. Here, the electronic circuitry 132 is fabricated in a silicon wafer which subsequently becomes the MEMS substrate 130 supporting a spherically focused transducer 133 formed from a film of piezoelectric polymer located on the wide portion of the substrate located at the distal end of the MEMS 130. This monolithic structure 130 is functionally equivalent to the ASIC/MEMS hybrid 138 illustrated in FIG. 4A, while offering the simplicity and convenience of a monolithic structure and eliminating the need for flip-chip bonding of the ASIC and MEMS components. However, the monolithic approach adds complexity to the manufacturing process since both the ASIC and MEMS features and related processing techniques must coexist on a single wafer without interfering with one other. Furthermore, as will be illustrated subsequently, it may be advantageous to separate the electronic circuitry (ASIC) from the transducer (MEMS) in order to facilitate mounting the transducer at the appropriate angle to enable Doppler color flow imaging.

For the PMUT device, any scheme for electrical connection between the ASIC and MEMS or for lead attachment between the cable and the ASIC/MEMS hybrid assembly must take into consideration the temperature sensitivity of the polymer piezoelectric material. The piezoelectric copolymer poly(vinylidene difluoride-trifluoroethylene) or p(VDF-TrFE) material preferred for the PMUT application must be kept at or below 140° C. under all circumstances in order to prevent degradation of the material properties. Once the device is fabricated, the temperature should more preferably be kept below 100° C. to avoid thermal stress on the polymer film or damage to the transducer structure. Furthermore, once the piezoelectric copolymer is poled, the temperature should be kept below 80° C. and more preferably below 50° C. in order to prevent loss of polarization and consequent reduction of the electromechanical coupling coefficient. These temperature constraints place significant limitations on the electrical attachment techniques that can be used for connecting to the MEMS device that includes the transducer. To a lesser extent, these temperature constraints may also limit the techniques that can be used for forming electrical connections between the ASIC and to the cable. For electrical connection to the MEMS component, some viable techniques include silver-epoxy or similar conductive adhesive that can be cured at less than 80° C. and more preferably below 50° C., light-curable (using ultraviolet or other wavelengths) conductive adhesives, anisotropic conductive adhesives or films based on low-temperature-curable or light-curable adhesives, mechanical contacts, low temperature ultrasonic wire-bonding, and low temperature (indium-based) solders.

Figure 5:
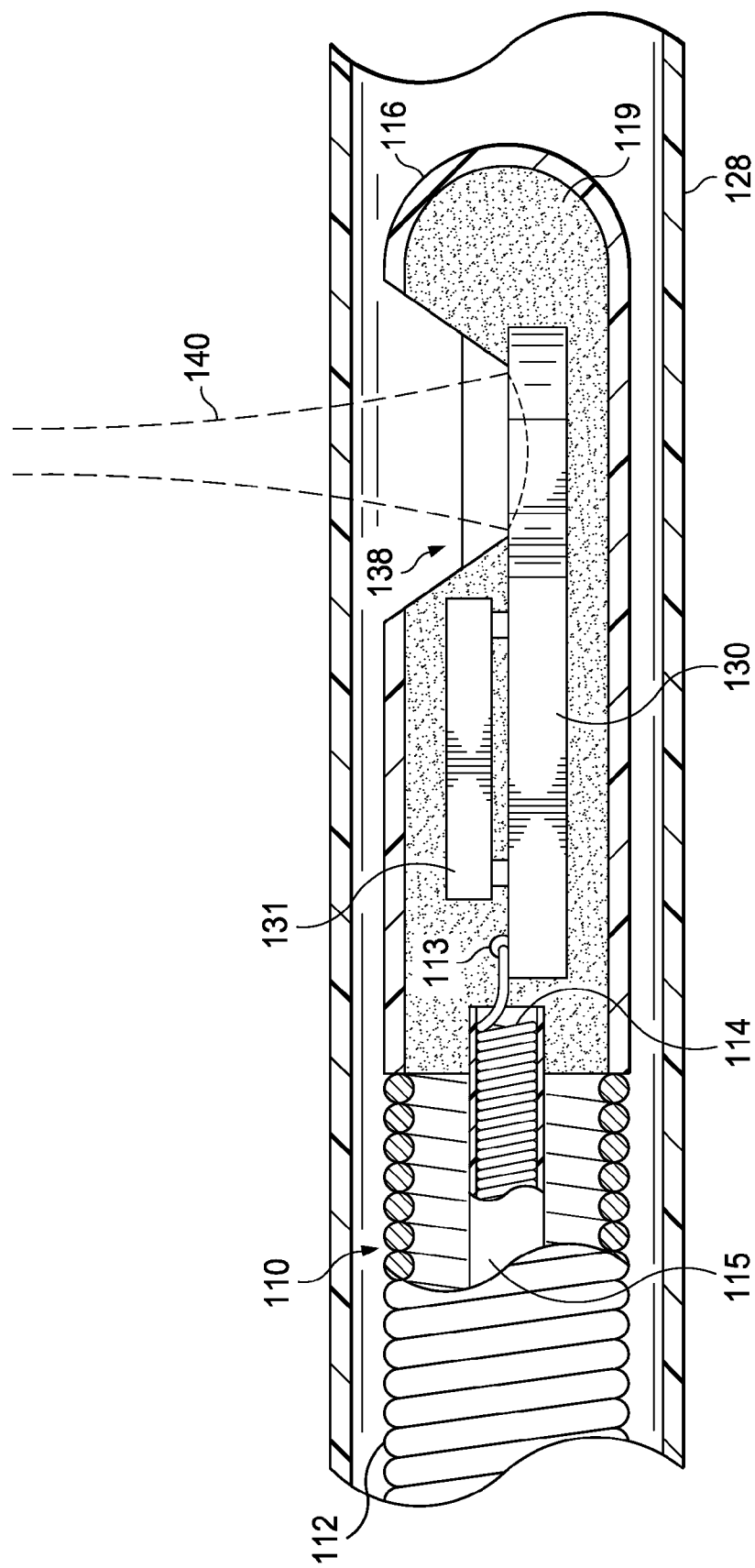
FIG. 5 is an illustration of a rotational IVUS transducer configuration utilizing a polymer piezoelectric micromachined ultrasound transducer wherein the transducer, electronic circuit, and housing are disposed at the end of the imaging core and inside the catheter sheath which is positioned within the vessel of interest.

FIG. 5 shows a cross-sectional side view of a distal portion of the catheter 102 incorporating the PMUT ASIC/MEMS hybrid assembly illustrated in FIG. 4B. In the illustrated embodiment, the imaging core 110 is terminated at its distal tip by a housing 116 fabricated from stainless steel and provided with a rounded nose and a cutout for the ultrasound beam 140 to emerge. The flexible driveshaft 112 of the imaging core 110 is composed of two or more layers of counter wound stainless steel wires, welded, or otherwise secured to the housing 116 such that rotation of the flexible driveshaft also imparts rotation on the housing 116. An electrical cable 114 with an optional shield 115 is attached to a PMUT ASIC/MEMS hybrid assembly 138, and the electrical cable 114 extends through an inner lumen of the flexible driveshaft 112 to the proximal end of the imaging core 110 where it is terminated to the electrical connector portion of the rotational interface 111 shown in FIG. 2. The ASIC/MEMS hybrid assembly 138 is secured in place within the housing 116 by epoxy 119 or similar bonding agent, which also serves as an acoustic backing material to absorb acoustic reverberations within the housing 116 and as a strain relief for the electrical cable 114 where it is attached to the MEMS substrate 130.

While FIG. 5 illustrates the incorporation of an advanced technology PMUT device into the imaging core of a rotational IVUS catheter, the generally planar nature of the PMUT ASIC/MEMS hybrid assembly 138, and its relatively long aspect compared to the imaging core diameter, makes it impractical to tilt the assembly at the substantial angle (10° to 30°) required for robust Doppler color flow imaging. Accordingly, there is a need for an improved configuration for the ASIC/MEMS hybrid assembly to facilitate mounting the transducer at the modest tilt angle required for Doppler color flow imaging.

Figure 6:
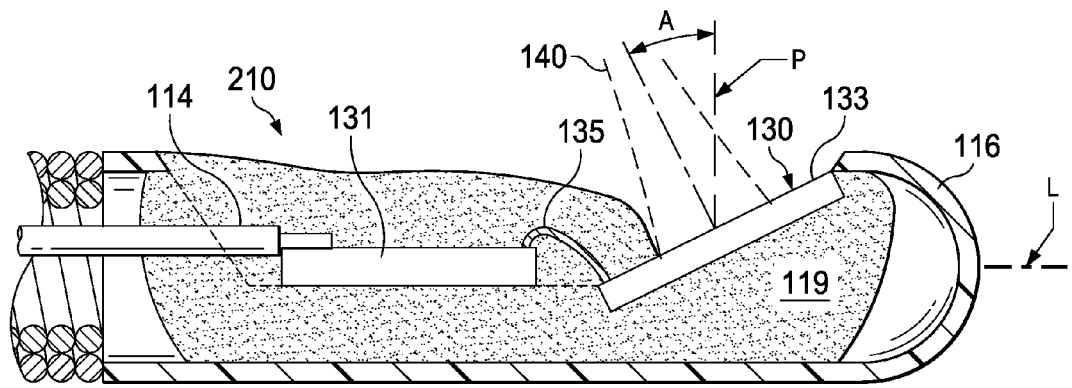
FIG. 6 is an illustration of a rotational IVUS transducer configuration utilizing a polymer piezoelectric micromachined ultrasound transducer wherein the transducer, electronic circuit, and housing are disposed at the end of the imaging core and inside the catheter sheath which is positioned within the vessel of interest. This configuration uses wire bonding to connect the transducer to the electronic circuit to facilitate mounting the transducer at a substantial tilt angle, thereby enabling the collection of Doppler ultrasound blood flow data.

Referring now to FIG. 6, shown therein is a cross-sectional side view of a distal portion of an imaging core 210 according to one preferred embodiment of the present disclosure. The imaging core 210 may be similar to the imaging core 110 of catheter 102 described above. In that regard, the imaging core 210 includes features and functionality similar to those discussed above with respect to imaging core 110. Accordingly, the same reference numerals have been utilized to refer to analogous features. For example, the imaging core 210 includes a MEMS 130 having a spherically-focused transducer 133 formed thereon and an ASIC 131 electrically coupled to the MEMS 130. However, in the exemplary configuration of FIG. 6, the ASIC 131 and MEMS 130 are wire-bonded together by wires 135 to form the electrical connections between the two components and mounted to the transducer housing 116 using epoxy 119 or similar bonding agent. This epoxy 119 also serves as an acoustic backing material to absorb acoustic reverberations within the housing 116, as a strain relief for the electrical cable 114 where it is attached to the ASIC 131, and as electrical insulation to isolate the electrical circuitry from contact with the saline or other fluid that fills the catheter lumen and surrounds the imaging core. The leads of the cable 114 are soldered, welded, or otherwise electrically coupled to the ASIC 131. In this exemplary embodiment, the MEMS component 130 shown in FIG. 6 is a truncated version of the paddle-shaped device shown in FIG. 4A, with the narrow "handle" portion of the paddle removed. Wires 135 interconnect ASIC 131 with MEMS component 130. One advantage of the wire-bonding approach is that, as a consequence of its relatively short aspect, the MEMS 130 carrying the PMUT transducer 133 can be mounted at an oblique angle with respect to the longitudinal axis of the housing 116 and the imaging core 210 such that the ultrasound beam 140 propagates at a modest angle A with respect to a perpendicular P to the central longitudinal axis L of the imaging device. This tilt angle helps to diminish the sheath echoes that can reverberate in the space between the transducer and the catheter sheath 128, and it also facilitates Doppler color flow imaging as disclosed in the co-pending application referenced above.

Figure 7:
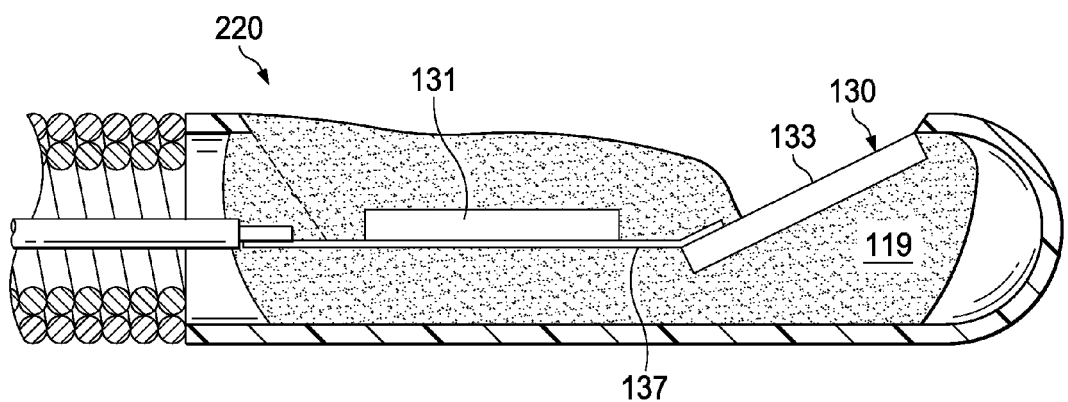
FIG. 7 is an illustration of a rotational IVUS transducer configuration utilizing a polymer piezoelectric micromachined ultrasound transducer wherein the transducer, electronic circuit, and housing are disposed at the end of the imaging core and inside the catheter sheath which is positioned within the vessel of interest. This configuration uses a flex circuit to connect the transducer to the electronic circuit to facilitate mounting the transducer at a substantial tilt angle, thereby enabling the collection of Doppler ultrasound blood flow data.

Referring now to FIG. 7, shown therein is a cross-sectional side view of a distal portion of an imaging core 220 according to another preferred embodiment of the present disclosure. The imaging core 220 may be similar to the imaging core 110 of catheter 102 described above. In that regard, the imaging core 220 includes features and functionality similar to those discussed above with respect to imaging core 110. Accordingly, the same reference numerals have again been utilized to refer to analogous features. In the exemplary configuration of FIG. 7, each of the electrical cable 114, the ASIC 131, and the MEMS 130 are welded, soldered, bonded, and/or otherwise electrically coupled to the flex circuit substrate 137 such that conductors within the flex circuit 137 carry signals among the conductors of the electrical cable 114, the ASIC 131, and the MEMS 130 to facilitate operation of the imaging core 220. The flex circuit assembly is then mounted to the transducer housing 116 using epoxy 119 or similar bonding agent. This epoxy 119 also serves as an acoustic backing material to absorb acoustic reverberations within the housing 116, as a strain relief for the electrical cable 114 where it is attached to the flex circuit, and as electrical insulation to isolate the electrical circuitry from contact with the saline or other fluid that fills the catheter lumen and surrounds the imaging core. For this configuration, the MEMS component 130 is preferably a truncated version. The flex circuit approach shares the advantage of the wire-bonded approach of FIG. 6, in that as a consequence of its relatively short aspect, the MEMS 130 carrying the PMUT transducer 133 can be mounted at an oblique angle with respect to the longitudinal axis of the housing 116 and the imaging core 220 such that the ultrasound beam 140 propagates at a modest angle with respect to a perpendicular to the central longitudinal axis of the imaging device. This tilt angle helps to diminish the sheath echoes that can reverberate in the space between the transducer and the catheter sheath 128, and it also facilitates Doppler color flow imaging as disclosed in the co-pending application referenced above.

Figure 8:
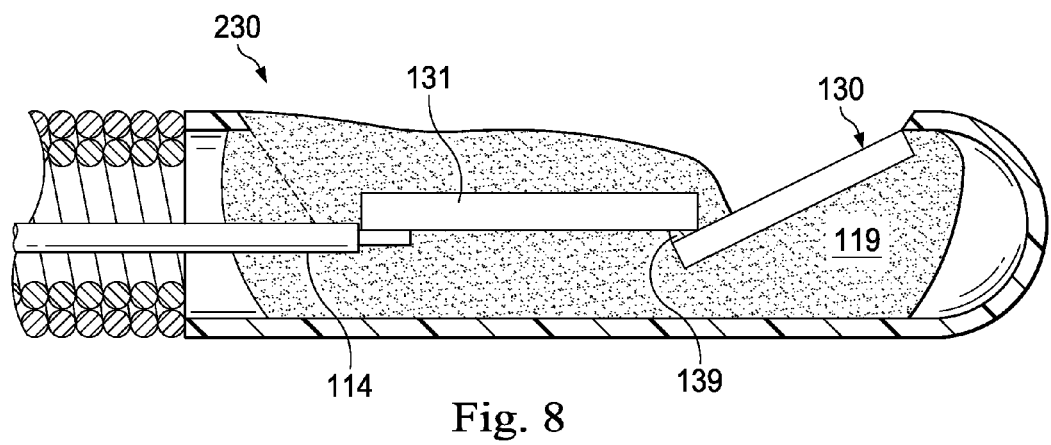
FIG. 8 is an illustration of a rotational IVUS transducer configuration utilizing a polymer piezoelectric micromachined ultrasound transducer wherein the transducer, electronic circuit, and housing are disposed at the end of the imaging core and inside the catheter sheath which is positioned within the vessel of interest. This configuration uses bumps on the bond pads with silver epoxy bonding to connect the transducer to the electronic circuit to facilitate mounting the transducer at a substantial tilt angle, thereby enabling the collection of Doppler ultrasound blood flow data.

Referring now to FIG. 8, shown therein is a cross-sectional side view of a distal portion of an imaging core 230 according to another preferred embodiment of the present disclosure. The imaging core 230 may be similar to the imaging core 110 of catheter 102 described above. In that regard, the imaging core 230 includes features and functionality similar to those discussed above with respect to imaging core 110. Accordingly, the same reference numerals have again been utilized to refer to analogous features. In the exemplary configuration of FIG. 8, the ASIC 131 and the MEMS 130 are bonded together with two small dots of silver epoxy 139 to form the electrical connections between the components and then reinforced with additional non-conductive epoxy material. The leads of the cable 114 are soldered, welded, or otherwise electrically coupled to the ASIC 131, either before or after the ASIC 131 and MEMS 130 are bonded together. Once this ASIC/MEMS hybrid assembly has cured, it can be mounted within the transducer housing 116 using additional epoxy 119 or similar bonding agent. This epoxy 119 also serves as an acoustic backing material to absorb acoustic reverberations within the housing 116, as a strain relief for the electrical cable 114 where it is attached to the ASIC 131, and as electrical insulation to isolate the electrical circuitry from contact with the saline or other fluid that fills the catheter lumen and surrounds the imaging core. In this exemplary embodiment, the MEMS 130 is a truncated version, and furthermore, the bonding pads on the MEMS 130 may include bumps formed thereon according to known methods. In this case, the geometry of the bumps and the ASIC bonding pads will cause the MEMS component to be attached to the ASIC at an oblique angle, with the angle controlled by the bump height. This ASIC/MEMS hybrid assembly bonding approach shares the advantage of the wire-bonded approach of FIG. 6 and the flex circuit approach of FIG. 7, in that as a consequence of its relatively short aspect, the MEMS 130 carrying the PMUT transducer 133 can be mounted at an oblique angle with respect to the longitudinal axis of the housing 116 and the imaging core 230 such that the ultrasound beam 140 propagates at a modest angle with respect to a perpendicular to the central longitudinal axis of the imaging device. This tilt angle helps to diminish the sheath echoes that can otherwise reverberate in the space between the transducer and the catheter sheath 128, and it also facilitates Doppler color flow imaging as disclosed in the co-pending application referenced above.

Figure 9:
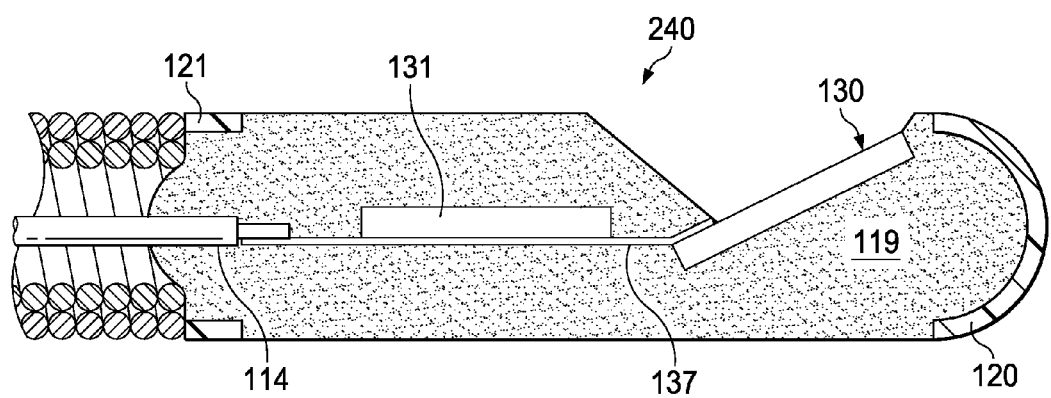
FIG. 9 is an illustration of a rotational IVUS transducer configuration utilizing a polymer piezoelectric micromachined ultrasound transducer wherein the transducer, electronic circuit, and housing are disposed at the end of the imaging core and inside the catheter sheath which is positioned within the vessel of interest. This configuration uses a molded transducer housing together with a flex circuit to connect the transducer to the electronic circuit to facilitate mounting the transducer at a substantial tilt angle, thereby enabling the collection of Doppler ultrasound blood flow data.

For any of the ASIC/MEMS hybrid assembly configurations describe in FIGS. 7, 8, and 9, the stainless steel housing element and the epoxy filler material can be replaced by a molded housing of similar shape. It is possible to place an ASIC/MEMS hybrid assembly inside of a mold, and then fill the mold with a polymer material, possibly the same epoxy used to fill the stainless steel housings of the aforementioned configurations. Alternatively, the mold material may be another composition that provides a favorable combination of acoustic properties where it acts as an acoustic backing material to dampen reverberations within the housing, mechanical properties where it serves to provide strength and lubricity to the mechanical structure of the housing, and molding properties where it provides the desired flow and curing properties for this type of insert micro-molding. A related technology for molding the transducer housing of a conventional PZT-based rotational IVUS catheter is disclosed in application US 2010/0160788 A1 which is incorporated herein by reference in its entirety.

Referring now to FIG. 9, shown therein is a cross-sectional side view of a distal portion of an imaging device 240 according to another preferred embodiment of the present disclosure. The imaging core 240 may be similar to the imaging core 110 of catheter 102 described above. In that regard, the imaging core 240 includes features and functionality similar to those discussed above with respect to imaging core 110. Accordingly, the same reference numerals have again been utilized to refer to analogous features. In the exemplary configuration of FIG. 9, each of the electrical cable 114, the ASIC 131, and the MEMS 130 are welded, soldered, bonded, and/or otherwise electrically coupled to the flex circuit substrate 137 such that conductors within the flex circuit 137 carry signals among the conductors of the electrical cable 114, the ASIC 131, and the MEMS 130 to facilitate operation of the imaging core 240. The flex circuit assembly is then placed in a mold along with optional nosecone 120 and optional weld ring 121 inserts, and the mold is filled with epoxy 119 or similar material to secure the components and to form the molded housing. Besides forming the mechanical structure of the molded housing, this epoxy 119 also serves as an acoustic backing material to absorb acoustic reverberations within the housing 116, as a strain relief for the electrical cable 114 where it is attached to the flex circuit, and as electrical insulation to isolate the electrical circuitry from contact with the saline or other fluid that fills the catheter lumen and surrounds the imaging core. The nosecone 120 provides a smooth round surface at the tip of the imaging core to minimize friction as the imaging core is rotated and advanced through the catheter lumen. The weld ring 121 serves as an attachment feature where the flexible drive cable can be secured by laser welding or similar method to the molded housing assembly. The flexible drive cable can be attached to the weld ring either before or after the housing is molded. For this configuration, the MEMS component 130 is preferably a truncated version. The molded housing approach shares the same advantage of the stainless steel housing approaches of FIGS. 6, 7, and 8, in that as a consequence of its relatively short aspect, the MEMS 130 carrying the PMUT transducer 133 can be mounted at an oblique angle with respect to the longitudinal axis of the housing 116 and the imaging core 240 such that the ultrasound beam 140 propagates at a modest angle with respect to a perpendicular to the central longitudinal axis of the imaging device. This tilt angle helps to diminish the sheath echoes that can reverberate in the space between the transducer and the catheter sheath 128, and it also facilitates Doppler color flow imaging as disclosed in the co-pending application discussed above.

Referring now to FIGS. 10-16, shown therein are aspects of transducer structural designs and mounting arrangements that are particularly suited for utilizing a polymer-based PMUT within a rotational IVUS imaging system according to embodiments of the present disclosure. In that regard, some structural designs of the PMUT and, in particular, the PMUT substrates and/or support structures, such as the MEMS components described above, are configured to facilitate mounting of the transducer at an oblique angle with respect to the central longitudinal axis of the intravascular device while keeping the PMUT substrate and/or support structure within an outer profile defined by the intravascular device. In some instances, the PMUT substrate and/or support structure is kept within an outer profile defined by a transducer housing coupled to a flexible elongate member of the intravascular device. More particularly, in some embodiments the transducer housing defines a circular outer profile that the PMUT substrate and/or support structure does not extend radially beyond. By keeping the PMUT substrate and/or support structure within the outer profile of the transducer housing, any potential friction, kinking, and/or other problems that might arise from the PMUT substrate and/or support structure contacting the surrounding catheter during rotation are prevented. Further, as noted above, mounting the ultrasound transducer at an oblique angle results in the ultrasound beam propagating at an oblique angle with respect to a perpendicular to the central longitudinal axis of the imaging core, which can diminish sheath echoes and facilitate Doppler color flow imaging.

Referring more specifically to FIGS. 10-12, shown therein are aspects of mounting a PMUT MEMS 500 having a rectangular outer profile at an oblique angle within an intravascular imaging device. As shown in FIG. 10, the PMUT MEMS 500 comprises a substrate or support structure 502 in which a spherically focused transducer 504 is formed. The PMUT MEMS substrate 502 has a rectangular outer profile. FIG. 11 shows the PMUT MEMS 500 mounted within a transducer housing 506 of an intravascular device. For sake of clarity with respect to the structural mounting arrangement of the PMUT MEMS 500 within the transducer housing 506, the other components of the intravascular device that would also be positioned within the transducer housing (e.g., epoxy or other adhesive used for mounting the PMUT MEMS 500, conductors coupled to the PMUT MEMS 500, ASIC, and/or other components) have been omitted from FIG. 11, but it is understood that one, some, or all of these components are present in some embodiments. Further, transducer housing 506 has one or more features similar to the housings described above in some instances that will not be discussed at this time. As shown in FIG. 11, the PMUT MEMS 500 is mounted at an oblique angle with respect to a central longitudinal axis 508 of the transducer housing 506. In that regard, in some implementations the PMUT MEMS 500 is mounted at an oblique angle between about 10 degrees and about 30 degrees.

Referring more specifically to FIG. 12, the transducer housing 506 defines an outer profile 510. In the illustrated embodiment, the outer profile 510 is circular. In that regard, the circular outer profile 510 of the illustrated embodiment has a diameter 512. In some implementations the diameter 512 of the sensor housing 506 sized and shaped to fit within a central lumen of a catheter sheath or guiding catheter. As shown in FIG. 15, with the PMUT MEMS 500 mounted at an oblique angle within the transducer housing 506 there is the possibility for upper corners 514, 516 of the PMUT MEMS 500 to extend radially beyond the outer profile 510 of the transducer housing 506. The distance the PMUT MEMS 500 extends radially beyond the outer profile 510 of the transducer housing 506 is dependent on the structural size of the PMUT MEMS 500 (i.e., height, width, and length), the mounting angle of the PMUT MEMS 500 within the transducer housing, and the structural size of the transducer housing 506 (i.e., outer profile diameter, inner lumen diameter, and cutout/opening size and profile). Generally, with a fixed PMUT MEMS structural arrangement, the greater the mounting angle of the PMUT MEMS 500 the greater the likelihood that the corners 514, 516 will extend radially beyond the outer profile 510 of the transducer housing 506. Accordingly, in order to keep the PMUT MEMS 500 within the outer profile 510 of the transducer housing 506 the mounting angle of the PMUT MEMS 500 may be limited to angles less than a desired mounting angle. FIGS. 13-16 below illustrate alternative implementations of PMUT MEMS that increase the range of available mounting angles without causing the PMUT MEMS to extend radially beyond the outer profile 510 of the transducer housing 506.

Referring now to FIG. 13, shown therein are aspects of mounting the PMUT MEMS 130 and ASIC 144, similar to those described above with respect to FIGS. 6-9, within the transducer housing 116 at an oblique angle. For sake of clarity with respect to the structural mounting arrangement of the PMUT MEMS 130 and ASIC 144 within the transducer housing 116, the other components of the intravascular device that would also be positioned within the transducer housing (e.g., epoxy or other adhesive used for mounting the PMUT MEMS 130 and ASIC 144, conductors coupled to the PMUT MEMS 130 and/or ASIC 144, flex circuits, and/or other components) have been omitted from FIG. 13, but it is understood that one, some, or all of these components are present in some embodiments. As shown in FIGS. 6-9, the PMUT MEMS 130 is mounted at an oblique angle with respect to a central longitudinal axis of the transducer housing 116. In that regard, in some implementations the PMUT MEMS 130 is mounted at an oblique angle between about 10 degrees and about 30 degrees. With the PMUT MEMS 130 mounted at an oblique angle within the transducer housing 116 the arcuate profile 520 of the PMUT MEMS substrate prevents the PMUT MEMS 130 from extending radially beyond the circular outer profile 510 of the transducer housing 116 having a diameter 512. The relative spacing of the outer profile of the PMUT MEMS 130 from the outer profile 510 of the transducer housing 116 is dependent on the structural size of the PMUT MEMS 130 (i.e., height, width, length, arcuate profile of widened portion, etc.), the mounting angle of the PMUT MEMS 130 within the transducer housing, and the structural size of the transducer housing 116 (i.e., outer profile diameter, inner lumen diameter, and cutout/opening size and profile). In the illustrated embodiment, the PMUT MEMS 130 has a tombstone shape with three linear boundaries and an arcuate distal boundary 520.

In some embodiments, the arcuate profile 520 of the distal boundary of the PMUT MEMS 130 substrate has a constant radius of curvature. In some implementations the radius of curvature of the arcuate profile 520 is equal to or less than the radius of curvature of the circular outer profile 510 of the transducer housing 116. However, in other implementations the radius of curvature of the arcuate profile 520 is greater than the radius of curvature of the circular outer profile 510 of the transducer housing 116. In that regard, in some instances the particular radius of curvature for the arcuate profile 520 is selected based on the desired mounting angle for the PMUT MEMS 130 and structural features of the transducer housing 116 to ensure that the PMUT MEMS 130 does not extend radially beyond the outer profile 510 when mounted within the transducer housing 116. To that end, in some implementations the arcuate profile 520 has a variable radius of curvature along its length. With the arcuate profile 520 of the PMUT MEMS 130 substrate maintaining the PMUT MEMS 130 within the outer profile 510 defined by the transducer housing 116 any potential friction, kinking, and/or other problems that might arise from the PMUT substrate and/or support structure contacting the surrounding catheter during rotation are prevented.

Figure 14:
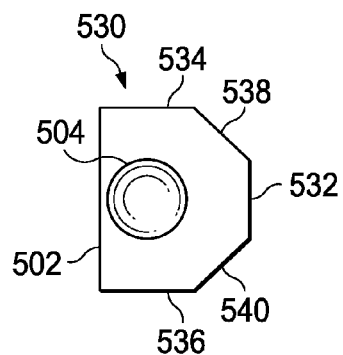
FIG. 14 is a diagrammatic top view of a PMUT MEMS component according to an embodiment of the present disclosure.
Figure 15:
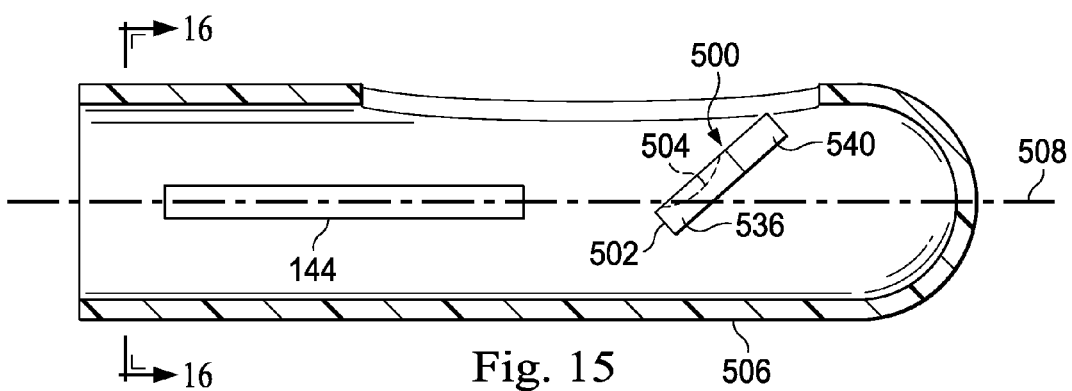
FIG. 15 is a diagrammatic, cross-sectional side view of a distal portion of an imaging device incorporating the PMUT MEMS component of FIG. 14 according to an embodiment of the present disclosure.
Figure 16:
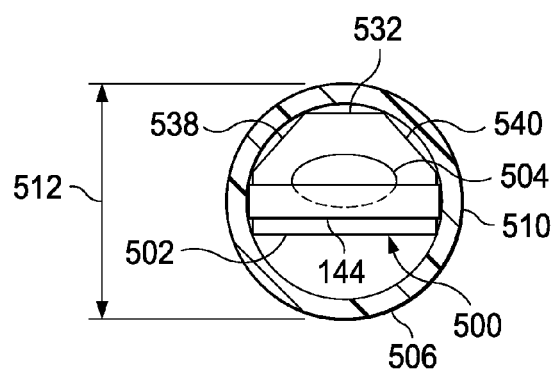
FIG. 16 is a diagrammatic, cross-sectional end view of the distal portion of the imaging device of FIG. 15 taken along section line 16-16.

Referring now to FIGS. 14-16, shown therein are aspects of mounting a PMUT MEMS 530 having an outer profile configured to facilitate mounting at an oblique angle within an intravascular imaging device. As shown in FIG. 14, the PMUT MEMS 530 comprises a substrate or support structure 502 in which a spherically focused transducer 504 is formed. The PMUT MEMS substrate 502 has a generally rectangular outer profile, but with a distal portion of PMUT MEMS substrate having tapered corners. In that regard, a distal end boundary 532 of the PMUT MEMS substrate 502 extends substantially perpendicular to side boundaries 534, 536 similar to a traditional rectangular substrate profile. However, the transitions between the side boundaries 534, 536 are tapered to reduce the radial profile of the PMUT MEMS 530 when mounted at an oblique angle within the transducer housing 506. In particular, an outer boundary 538 extends between the side boundary 534 and the end boundary 532. While the outer boundary 538 extends at an oblique angle with respect to both the side boundary 534 and the end boundary 532, the particular dimensions of the outer boundary 538 (i.e., length and angle(s) with respect to the side and end boundaries) can be selected based on various factors, including without limitations the desired mounting angle of the PMUT MEMS 530 within the transducer housing, the structural size of the transducer housing 506 (i.e., outer profile diameter, inner lumen diameter, and cutout/opening size and profile), and/or other factors. Likewise, an outer boundary 540 extends between the side boundary 536 and the end boundary 532. While the outer boundary 540 extends at an oblique angle with respect to both the side boundary 536 and the end boundary 532, the particular dimensions of the outer boundary 540 (i.e., length and angle(s) with respect to the side and end boundaries) can be selected based on various factors, including without limitations the desired mounting angle of the PMUT MEMS 530 within the transducer housing, the structural size of the transducer housing 506 (i.e., outer profile diameter, inner lumen diameter, and cutout/opening size and profile), and/or other factors. In that regard, in some implementations that the outer boundaries 538 and 540 have symmetrical profiles, such as in the illustrated embodiment. In other implementations, the outer boundaries 538 and 540 do not have symmetrical profiles.

FIG. 15 shows the PMUT MEMS 530 mounted within the transducer housing 506 of an intravascular device. For sake of clarity with respect to the structural mounting arrangement of the PMUT MEMS 530 within the transducer housing 506, the other components of the intravascular device that would also be positioned within the transducer housing (e.g., epoxy or other adhesive used for mounting the PMUT MEMS 530, conductors coupled to the PMUT MEMS 530, ASIC, and/or other components) have been omitted from FIG. 15, but it is understood that one, some, or all of these components are present in some embodiments. As shown in FIG. 15, the PMUT MEMS 530 is mounted at an oblique angle with respect to a central longitudinal axis 508 of the transducer housing 506. In that regard, in some implementations the PMUT MEMS 530 is mounted at an oblique angle between about _ degrees and about _ degrees. Referring more specifically to FIG. 16, with the PMUT MEMS 530 mounted at an oblique angle within the transducer housing 506 the tapered corners of the PMUT MEMS 530 defined by boundaries 538 and 540 prevent the PMUT MEMS 530 from extend radially beyond the outer profile 510 of the transducer housing 506. The relative spacing of the outer profile of the PMUT MEMS 530 from the outer profile 510 of the transducer housing 506 is dependent on the structural size of the PMUT MEMS 530 (i.e., height, width, and length), the mounting angle of the PMUT MEMS 530 within the transducer housing, and the structural size of the transducer housing 506 (i.e., outer profile diameter, inner lumen diameter, and cutout/opening size and profile). With the PMUT MEMS 530 maintained within the outer profile 510 defined by the transducer housing 506 any potential friction, kinking, and/or other problems that might arise from the PMUT substrate and/or support structure contacting the surrounding catheter during rotation are prevented.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A rotational intravascular ultrasound (IVUS) system, comprising:
   an imaging device comprising:
      a flexible elongate member;
      an elongate housing coupled to a distal portion of the flexible elongate member, the elongate housing defining a circular outer profile;
      a piezoelectric micromachined ultrasound transducer (PMUT) mounted within the elongate housing at an oblique angle with respect to a central longitudinal axis of the elongate housing, wherein the PMUT is formed on a microelectromechanical system (MEMS) component sized and shaped such that the MEMS component does not extend beyond the circular outer profile of the elongate housing; and
      an application-specific integrated circuit (ASIC) electrically coupled to the PMUT adjacent to the distal portion of the flexible elongate member;
   an interface module configured to connect with a proximal connector of the imaging device; and
   an intravascular ultrasound (IVUS) processing component in communication with the interface module, wherein the IVUS processing component is configured to process data from the imaging device to measure a Doppler shift of blood flow through a vessel in which the imaging device is positioned, and to output the measured Doppler shift to a display.

2. The system of claim 1, wherein the ASIC includes:
   a pulser for selectively driving the PMUT,
   an amplifier for receiving and amplifying signals representative of ultrasound echoes received by the PMUT,
   a protection circuit configured to prevent the amplifier from receiving transmit pulses from the pulser and allow the amplifier to receive the echo signals from the PMUT, and
   timing and control circuitry for coordinating operation of the pulser, amplifier, and protection circuit.

3. The system of claim 1, wherein the MEMS component and the ASIC are electrically coupled to a flex circuit substrate.

4. The system of claim 3, wherein the ASIC is mounted parallel to the central longitudinal axis of the elongate housing.

5. The system of claim 1, wherein the MEMS component includes an outer boundary having an arcuate profile.

6. The system of claim 5, wherein the arcuate profile has a radius of curvature that is equal to or less than the radius of the circular outer profile of the elongate housing.

7. The system of claim 5, wherein the MEMS component has a first portion having only linear outer boundaries and a second portion that includes the outer boundary having the arcuate profile.

8. The system of claim 7, wherein the outer boundary having the arcuate profile is a distal boundary of the MEMS component.

9. The system of claim 8, wherein the MEMS component has a tombstone shape.

10. The system of claim 7, wherein the MEMS component has a paddle shape.

11. The system of claim 5, wherein the arcuate profile has a variable radius of curvature.

12. The system of claim 5, wherein the outer boundary having the arcuate profile is positioned adjacent to the circular outer profile of the elongate housing.

13. The system of claim 1, wherein the PMUT is mounted within the elongate housing at an oblique angle between 15° and 25° with respect to the central longitudinal axis of the elongate housing.

14. The system of claim 13, wherein the PMUT is oriented and configured to detect and measure between 26% and 42% of a theoretical maximum Doppler shift of blood flow substantially parallel to the central longitudinal axis of the elongate housing.

* * * * *